United States Patent
Zhang et al.

(10) Patent No.: US 7,468,394 B1
(45) Date of Patent: Dec. 23, 2008

(54) STERILE PHARMACEUTICAL COMPOSITION AND PROCESS FOR A SOLUTION OF PROPOFOL EMULSION HAVING MICROBIAL GROWTH RETARDATION

(75) Inventors: Jack Yongfeng Zhang, Rancho Cucamonga, CA (US); Mary Ziping Luo, Rancho Cucamonga, CA (US)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 1018 days.

(21) Appl. No.: 10/384,679

(22) Filed: Mar. 11, 2003

(51) Int. Cl.
*A61K 31/05* (2006.01)
*A61K 51/00* (2006.01)
*A61K 9/14* (2006.01)

(52) U.S. Cl. .................. 514/731; 424/1.21; 424/486
(58) Field of Classification Search ............... 454/486; 424/1.21, 486; 514/731
See application file for complete search history.

(56) References Cited

U.S. PATENT DOCUMENTS

| 5,496,818 | A  | * | 3/1996 | Schaupp et al. | ........... 514/225.8 |
| 6,254,853 | B1 | * | 7/2001 | Hendler et al. | ................ 424/45 |
| 6,399,087 | B1 | * | 6/2002 | Zhang et al.   | ............... 424/405 |

* cited by examiner

*Primary Examiner*—Raymond J Henley, III
(74) *Attorney, Agent, or Firm*—Albert O. Cota

(57) ABSTRACT

An oil-in-water propofol emulsion that contains soybean oil and egg lecithin, which provide a source of nutrition for microorganisms. Current products include additives to act as a microbial growth retardation agent, the processes described herein detail several methods for the optimization of the innate microbial retardation capability of propofol. Using this process improves the safety of a propofol emulsion solution by controlling microbial growth without the side effects associated with growth retardation additives.

9 Claims, 3 Drawing Sheets

STERILE PHARMACEUTICAL COMPOSITION AND PROCESS FOR A SOLUTION OF PROPOFOL EMULSION HAVING MICROBIAL GROWTH RETARDATION

TECHNICAL FIELD

The present invention generally pertains to processes for manufacturing a propofol emulsion that exhibits microbial retardation activity without the preservatives or additives. In particular the present invention provides processes for enhancing microbial growth retardation of propofol emulsion injectable by establishing or accelerating the equilibrium of propofol among aqueous phase, emulsion particles and liposome particles.

BACKGROUND ART

Propofol (2,6-Diisopropylphenol) is a well-known and widely used intravenous anesthetic agent. A significant advantage of using propofol is a rapid onset following infusion or bolus injection and the benefit of a very short recovery time, which requires minutes rather than hours. Propofol's hypnotic properties permit it to be used as both a sedative and to induce and maintain general anesthesia.

Chemically, propofol is a phenolic compound belonging to the same family. According to the Handbook of Pharmaceutical Excipient (Kibbe), phenols are mainly used as antimicrobial preservatives in parenteral pharmaceutical products. As a result of this, since propofol is the active agent and a phenolic compound, it could, under the optimal conditions, act as its own microbial retardation agent.

Propofol has limited water solubility, however it is easy to dissolve in soybean oil. As such, it must be incorporated with a solubilizing agent, surfactants or solvents to generate oil-in-water emulsions. The oil component of the emulsion is contained within a shell of the surfactants (egg lecithin), thus forming a "sunflower" structure, which can be seen in Table 1. Currently marketed propofol products are available as oil-in-water emulsions. The partition coefficient of propofol between soybean oil and water is 4,220 per our study for propofol.

DIPRIVAN® 1% consisting of 1% propofol, 10% soybean oil, 1.2% egg lecithin, and 2.25% glycerin, was originally released in 1989. However, within one year there were reports of an uncommonly high number of infections. Further investigation showed that despite the product labeling, various non-aseptic practices were being used (e.g., storing opened DIPRIVAN® for administration to multiple patients). As a result, the manufacturer altered the prescribing information to reinforce the need for aseptic handling, which includes immediate use after opening and one vial for each patient. While this change in the prescribing information and accompanying educational campaign did reduce the number of infections due to misuse, the problem was not completely solved. Despite the aforementioned efforts, in June 1993 another outbreak of infection was reported which included two deaths. The continued problems and high levels of infection caused the Food and Drug Administration (FDA) and Center for Disease Control (CDC) to suggest the re-formulation of the drug to provide antimicrobial activity; i.e., to prevent an increase of microorganism growth of no more than 10 fold in the time period at least 24 hours after adventitious, extrinsic contamination. This action was intended to reduce safety concerns associated with the injection of microbes into patients using the propofol emulsion solution.

In 1996, due to problems related to microbial growth in the soybean oil and egg lecithin, the original formulation was replaced by a new formulation that included the antimicrobial agent EDTA, as detailed by Jones, et al in U.S. Pat. No. 5,714,520. EDTA is a tetrabasic acid and a strong chelator of trace metals such as zinc. As a result, patients using DIPRIVAN® need to be monitored to ensure that zinc levels do not reach a point where zinc deficiency-related adverse affects occur. Also, in rare cases, the EDTA has been reported to have a toxic effect on renal tubes and patients should be periodically monitored in case signs of renal problems occur.

In 1999 another formulation of propofol entered the market. This formulation as detailed in U.S. Pat. No. 6,147,122 by Mirejovsky, et al includes sodium metabisulfite as a preservative. After an extensive testing process it was determined that sulfites can be included in oil-in-water emulsions in non-toxic amounts within the soluble phase without partitioning the organic phase or adversely effecting the formulation. While sodium metabisulfite does not inherently cause toxic side effects, it may cause allergic-type reactions including anaphylactic symptoms and life-threatening or less severe asthmatic episodes in certain susceptible people with sulfite sensitivity.

Ideally a formulation of propofol with increases safety would exist that provided microbial growth retardation activity without the side effects that are associated with the currently used additives (EDTA and sodium metabisulfate). Since propofol is a phenol, under optimal conditions it naturally provides microbial growth retardation activity.

The formulation described in U.S. Pat. No. 6,100,302 is an emulsion of Propofol that contains 1-3% of soybean oil to prevent against accidental microbial contamination during long-term IV infusions due to an increased availability of Propofol. However, the formulation containing 2% of soybean oil can not prevent a less than one log increase for E. coli at 48 hours.

Particularly, the formulation comprising 3% of soybean oil has more than a 10-fold increase for E. coli at 24 hours, which fails to meet current industry standards to prevent no more than one log increase in microbial growth at 24 hours. It appears that upon administration this formulation may also increase the problem of pain on injection due to a higher partition of Propofol in the aqueous phase. This has been studied by M. Eriksson, et al 1997.

In U.S. Pat. No. 6,399,087 Zhang, et al disclosed a propofol emulsion formulation with lower amounts of both soybean oil and egg lecithin and a lower pH. The formulation provides a base to enhance the phenol function of propofol itself, thus allowing the propofol to act as the microbial growth retardant agent. However, in order to get optimal microbial growth retardation, this type of additive-free formulation can reach suitable levels of propofol within the emulsion particles, the aqueous phase, and the liposome particles. The background included herein details the relative ease under which the emulsion particles and aqueous phase rapidly reach equilibrium with sufficient levels of propofol therein. However, it also details the slower equilibrium between the liposome particles and the aqueous phase, and processes for improving the dynamics of the equilibrium which improves the situation where the liposome particles is unacceptable as a nutritional source, in order to prevent the growth of microorganisms.

A search of the prior art did not disclose any patents that read directly on the claims of the instant invention, however the following U.S. patents are considered related:

| U.S. PAT. NO. | INVENTOR | ISSUED |
|---|---|---|
| 5,637,625 | Haynes | June 1997 |
| 5,714,520 | Jones, et al | February 1998 |
| 6,028,108 | George | February 2000 |
| 6,100,302 | Pejaver, et al | August 2000 |
| 6,147,122 | Mirejovsky, et al | November 2000 |
| 6,399,087 | Zhang, et al | January 2002 |
| OTHER PATENTS | | |
| WO99/396,96 | Mirejovsky, et al | August 1999 |
| WO00/243,76 | May, et al | May 2000 |

OTHER SOURCES

Kibbe, Arthur K. handbook of Pharmaceutical Excipient, $3^{rd}$ ed., Apha, Washington D.C.

DISCLOSURE OF THE INVENTION

The invention discloses:
(1) the importance of establishing a sufficient amount of propofol in liposome particles to reach microbial growth retardation of additive-free propofol emulsion injectable.
(2) propose several processes to establish or accelerate the equilibrium required to reach the necessary amount of propofol in liposome particles.

As detailed by Zhang et at (2002) the lower levels of egg lecithin and soybean oil in propofol emulsion formulation provide less growth medium for microorganisms. With less growth medium, a lower amount of microbial retardation activity is required. Propofol being a hindered phenol has the potential to provide microbial growth retardation activity, protecting the drug formulation from microorganism without the use of an additive, which may have side effects. By using the method detailed herein, a safely formulation can be produced wherein the microbial growth retardation is enhanced by establishing or accelerating the equilibrium of propofol among the aqueous phase, the emulsion particles and the liposomal shells.

These and other objects and advantages of the present invention will become apparent from the subsequent detailed description of the preferred embodiment and the appended claims taken in conjunction with the accompanying drawings.

BEST MODE FOR CARRYING OUT THE INVENTION

The best mode for carrying out the invention is presented in terms of a preferred embodiment for a sterile pharmaceutical composition and process for a solution of propofol emulsion having microbial growth retardation.

Figure 1:
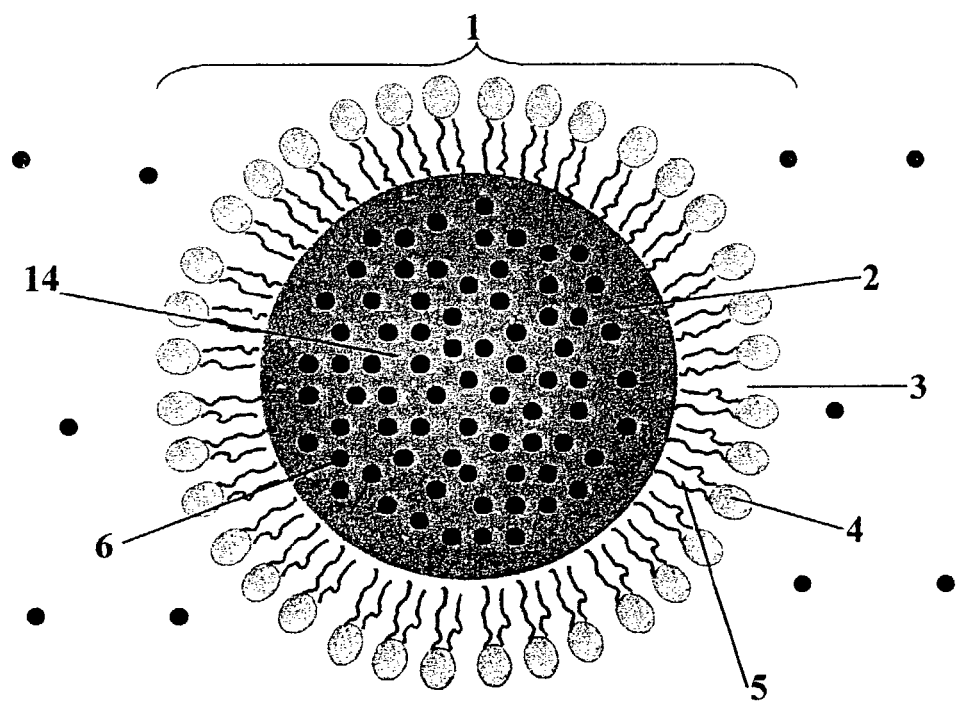
FIG. 1 is an illustration depicting the components that comprise the emulsion particles.
Figure 3:
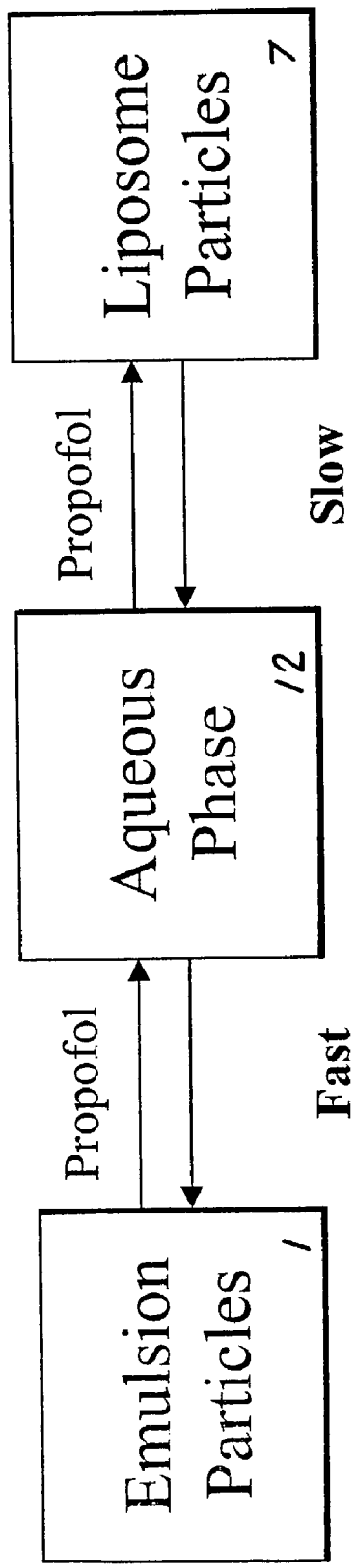
FIG. 3 is a block diagram showing the interaction of the propofol with the aqueous phase, the emulsion particles and the liposome particles.

The propofol emulsion solution consists of three components as shown in Table 1:

A) Emulsion particles, as shown in FIGS. 1 and 3: Emulsion particles 1 form a "sunflower" structure with a core 2 of oil 14 and propofol 6 contained within surfactant shell 3 of single layer surfactant, 200-400 nm or typically 210-340 nm. Most of the propofol contained in the emulsion solution is dissolved in the oil and forms the core of the emulsion particles. Egg lecithin has both a hydrophilic end, as shown as number 4 in FIG. 1 and a hydrophobic end, as shown an number 5 in FIG. 1.

Figure 2:
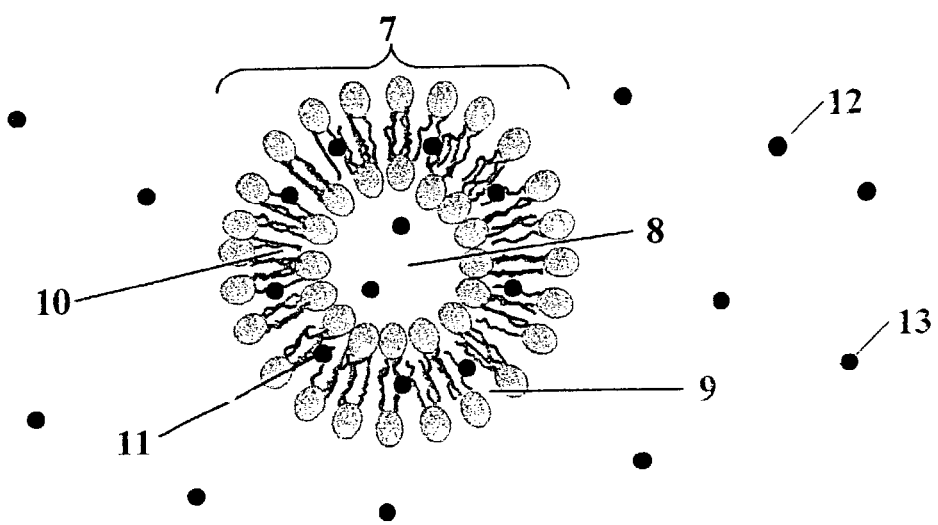
FIG. 2 is an illustration depicting the components that comprise the liposome particles.

B) Liposome particles, as shown in FIG. 2; Liposome particles 7 also form a "sunflower" structure, where the core 8 is made up of the aqueous phase contained within a surfactant shell of double layer surfactant 9, about 50-180 nm, typically 120-160 nm. The physical chemical behavior of the interval of the double layers is hydrophobic and is similar to oil. Propofol can also dissolve in the interval of the liposome shells, as shown in number 11 in FIG. 2. The propofol dissolved in the interval of the liposome shells, is also shown as number 10 in FIG. 2.

C) Aqueous phase, as shown in FIG. 2; The aqueous phase 12 acts as a support media for the emulsion solution. It is isotonic, determines the pH and contains free propofol 13.

The amount of propofol in each of the three components depends upon the formulation and manufacturing process. Herein, a comparison will be made between Diprivan® 1%, as a representation of the formulation used by Jones, et al, in U.S. Pat. No. 5,714,520 and Ampofol™, as an example of one particular formulation under the range covered by Zhang, et al in Pat. No. 6,399,087. The two formulations can be compared as follows:

| Formulation | 1% Diprivan ® | 1% Ampofol ™ |
|---|---|---|
| Propofol, Mg/mL | 10 | 10 |
| Soybean Oil, Mg/mL | 100 | 50 |
| Egg Lecithin, Mg/mL | 12 | 6 |
| Glycerin, Mg/mL | 22.5 | 22.5 |
| EDTA, Mg/mL | 0.05 | — |
| WFI | to 100% | to 100% |

The quantity or concentration of propofol within the emulsion particles is measured by weighing the core of emulsion particles. The quantity or concentration of propofol in the liposome particles is measured by the weight of the shell of the liposome particles.

The representative amounts of propofol within each of the three components are analyzed as follows:

TABLE 1

Concentration of Three Components in Propofol Emulsion

| Propofol Formulation | 1% Diprivan ® | 1% Ampofol ™ |
|---|---|---|
| Emulsion Core, % | 8.8-8.9 | 16.2-16.4 |
| Lipsome Shell, % | 4-6 | 10-15 |
| Aqueous Phase, mg/mL | 19.5 | 35.9 |

TABLE 2

Absolute Amount of Propofol Among Three Emulsions Components

| Item | 1% Diprivan ® | 1% Ampofol ™ |
|---|---|---|
| Weigh of Emulsion Core, mg/mL | 109.7-109.8 | 59.7-59.8 |
| Weight of Lecithin in Lipsome, mg/mL | 4.5 | 1.9 |
| Amount of propofol in Emulsion Core, mg/mL | 9.7-9.8 | 9.7-9.8 |
| Amount of propofol in Lipsome Lecithin, mg/mL | 0.2-0.3 | 0.2-0.3 |
| Amount of propofol in Aqueous Phase, mg/mL | 0.02 | 0.04 |

TABLE 3

Relative Distribution of Propofol Among Three Emulsion Components

| Propofol Formulation | 1% Diprivan ® | 1% Ampofol ™ |
|---|---|---|
| Emulsion Core, % | 97-98 | 97-98 |
| Lipsome Shell, % | 2-3 | 2-3 |
| Aqueous Phase, % | 0.2 | 0.4 |

However, most of the propofol in an injectable of the propofol emulsion lies within the emulsion core. Tables 2 and 3 list the absolute amount of propofol and the relative distribution of propofol among the three emulsion components, respectively.

Ampofol™ has a higher propofol concentration in the lipsome shell, but similar total propofol distributed throughout the shell due to the fact that Ampofol™ has only about 1.9 mg/mL of egg lecithin used to form the shell and Diprivan® has about 4.5 mg/mL, as listed in Table 2.

Establishing equilibrium between propofol in the emulsion particles and propofol in the aqueous phase is a rapid process. If an injectable of 1% propofol emulsion is diluted, the free propofol in the aqueous phase will immediately reduce. However, after a certain period of time, a new equilibrium will be established as detailed in Table 4.

TABLE 4

Equilibrium of Propofol between Aqueous Phase and Emulsion Particles

| | Oil Amount % | Dilution Factor | Free Propofol Immediately After Dilution µg/mL | Free Propofol at new Equilibrium µg/mL |
|---|---|---|---|---|
| Diprivan ® | 10 | 1 | 10.5 | — |
| | | 5 | 3.9 | 19.4 |
| | | 10 | 2.0 | 19.2 |
| | | 100 | 0.2 | 16.4 |
| Ampofol ™ | 5 | 1 | 35.9 | — |
| | | 5 | 7.2 | 35.4 |
| | | 10 | 3.6 | 34.7 |
| | | 100 | 0.4 | 26.5 |

Our study demonstrates that the new equilibrium between the emulsion particles and aqueous phase can be reached very quickly, specifically within a few minutes after the dilution. On the other hand, the equilibrium of propofol established between liposome particles and the aqueous phase is a much slower one. Based on our study, the propofol emulsion solution may take several months to reach equilibrium starting from a non-equilibrium state as will be further discussed herein.

The three components of propofol emulsion solution play various roles in microbial growth or growth retardation. In Table 5, Diprivan® (without EDTA) and Ampofol™ are used as examples to show the roles of the three emulsion components and their impact on retardation of microbial growth.

TABLE 5

Roles of the Three Emulsion Components on Microbial Growth

| Components | Support Growth | Retard Growth |
|---|---|---|
| Emulsion | Acceptable Nutrition Source e.g. Diprivan ® 1% | Unacceptable Nutrition Source e.g. Ampofol ™ 1% |
| Lipsome | Acceptable Nutrition Source e.g. Diprivan ® 1% | Unacceptable Nutrition Source e.g. Ampofol ™ 1% |
| Aqueous Phase | Acceptable Environment e.g. Diprivan ® 1% (no EDTA) | Unfavorable Environment e.g., Ampofol ™ 1%, e.g. Diprivan ® 1% (with EDTA) |

Two distinct strategies exist for establishing microbial growth retardation within an injectable of the propofol emulsion:

Strategy 1: An additive is introduced e.g. EDTA (U.S. Pat. No. 5,714,520), Pentetate (U.S. Pat. No. 6,208,108), or Sodium Metabisulfite (U.S. Pat. No. 6,147,122 and WO 99/396,96), to make the aqueous phase unacceptable for microbial growth. While effective as microbial growth retardation agent, these additives cause various side effects especially for patients in an intensive care unit (ICU). Also, when the injection of propofol emulsion requires dilution for administration (e.g. for NMR imaging, pediatric application, etc.), some formulations may lose their effectiveness for microbial growth retardation.

Strategy 2: The antimicrobial property of the propofol itself is used to make the emulsion and liposomal particles unacceptable as nutritional sources and make the aqueous phase unfavorable to support microbial growth. Namely, microorganisms have a very difficult time growing in an unfavorable environment and without an acceptable source of nutrition.

In order to comply with Strategy 2, it is necessary to make:
(1) emulsion particles unacceptable as a nutritional source, i.e, levels of propofol in the emulsion particles are high enough,
(2) liposome particles unacceptable as a nutritional source, i.e. levels of propofol in the liposome particles are high enough and
(3) the aqueous phase unfavorable, i.e., levels of propofol in the aqueous phase are high enough.

For Strategy 2 to be effective, all three times are necessary. According to existing literature, item (2) has never been realized. This is the reason why a propofol formulation with a very low amount of oil (3%), i.e. very high amounts of propofol in emulsion (25.0%) and free propofol in the aqueous phase (55 µg/mL), but with lower propofol in liposome, will have very poor microbial growth retardation, (log change=2.9 for E. coli after 24 hours of contamination (U.S. Pat. No. 6,100,302).

Items (1) and (3), as listed above, are very easy to achieve since reaching an equilibrium of propofol between the aqueous phase and emulsion particles (oil phase in emulsion) is a rapid process. These two items are almost solely dependent on the formulation used. However, item (2) is both formulation and process dependent since establishing equilibrium of propofol between the aqueous phase and liposome particles is dynamically very slow. The global dynamic character of propofol among the 3 components of propofol emulsion solution is summarized in FIG. 3.

When manufactured, the Propofol emulsion has Propofol within some of the liposomal shells and free propofol in the aqueous phase, or propofol outside the liposome shells. The liposomal spheres that do not have propofol or have significantly lower amounts of propofol within them than the equilibrium status make acceptable targets as a source of nutrition for an invading microorganism. By causing free propofol from the aqueous phase to migrate into the liposomal shells lacking propofol, the liposomes become less hospitable to invading microorganisms. The reduced free propofol will be compensated from the release of propofol from the emulsion cores. However, the movement of free-Propofol as it diffuses from the aqueous phase into the liposomal shell is time consuming, often requiring months to complete. In order for the process to be efficient, a way of speeding up this migration of free-Propofol is required. However, if a manufacturing process is specifically designed to entrap as much propofol as possible into the liposomal shell, i.e. very close to the equilibrium state, the slow diffusion can be avoided. Otherwise, an accelerated method for the improving the slow rate of diffusion is necessary.

Based on our research, it was discovered that heat is capable of encouraging the free-Propofol to move into the liposomal spheres.

The conventional process to make propofol emulsion injectable consist of several steps (denoted as Process T):

(1) mix organic phase: propofol, oil and egg lecithin,
(2) mix aqueous phase: water, glycerin,
(3) mix above two phases and adjust pH,
(4) emulsify by using a homogenizer,
(5) adjust final volume and pH,
(6) fill, close and seal,
(7) terminally sterilize,
(8) perform a candling procedure, and
(9) packaging.

Steps (1) to (3) may have different ways of mixing, such as mixing egg lecithin into the aqueous phase first, etc.

There are many ways to establish sufficient amounts of propofol within the liposome particles. The following are several examples:

EXAMPLE 1

At steps (1) and (3) a high speed mixer (immerge or in-line), such as 5,000-20,000 rpm or higher (normal 3,000 rpm), is used for pre-mixing. Control water amount in step (2) there should be no more than 3 times the volume of the organic phase. Due to the special pre-mixing at high speeds at a mixture with less water, more propofol will be distributed into liposome particles when the liposome particles initially form. This process will be denoted Process A.

EXAMPLE 2

After completing Process T, a step (10), holding products for three to six months or longer at room temperature to reach the natural equilibrium, is added after the step (9). This process will be denoted as Process B.

EXAMPLE 3

At step (7) a heating period, such as one to two hours at 100° C. or higher, will be combined with the normal autoclave cycle to accelerate the equilibrium of propofol between aqueous phase and the liposome particles. This process will be denoted as Process C.

A set of process C at different heating time for Ampofol was performed and the amounts of propofol in liposome shell were analyzed.

Table 6 lists the experimental results of the amount of propofol in liposome shell for Ampofol at different heating time at 121° C.

TABLE 6

Amount of Propofol in Liposome shell for Ampofol

| Heating Time (minutes) | Propofol Amount (%) |
| --- | --- |
| 0 | 7.4 |
| 20 | 9.2 |
| 60 | 13.1 |
| 120 | 14.2 |
| 180 | 13.7 |
| 240 | 13.9 |

Figure 4:
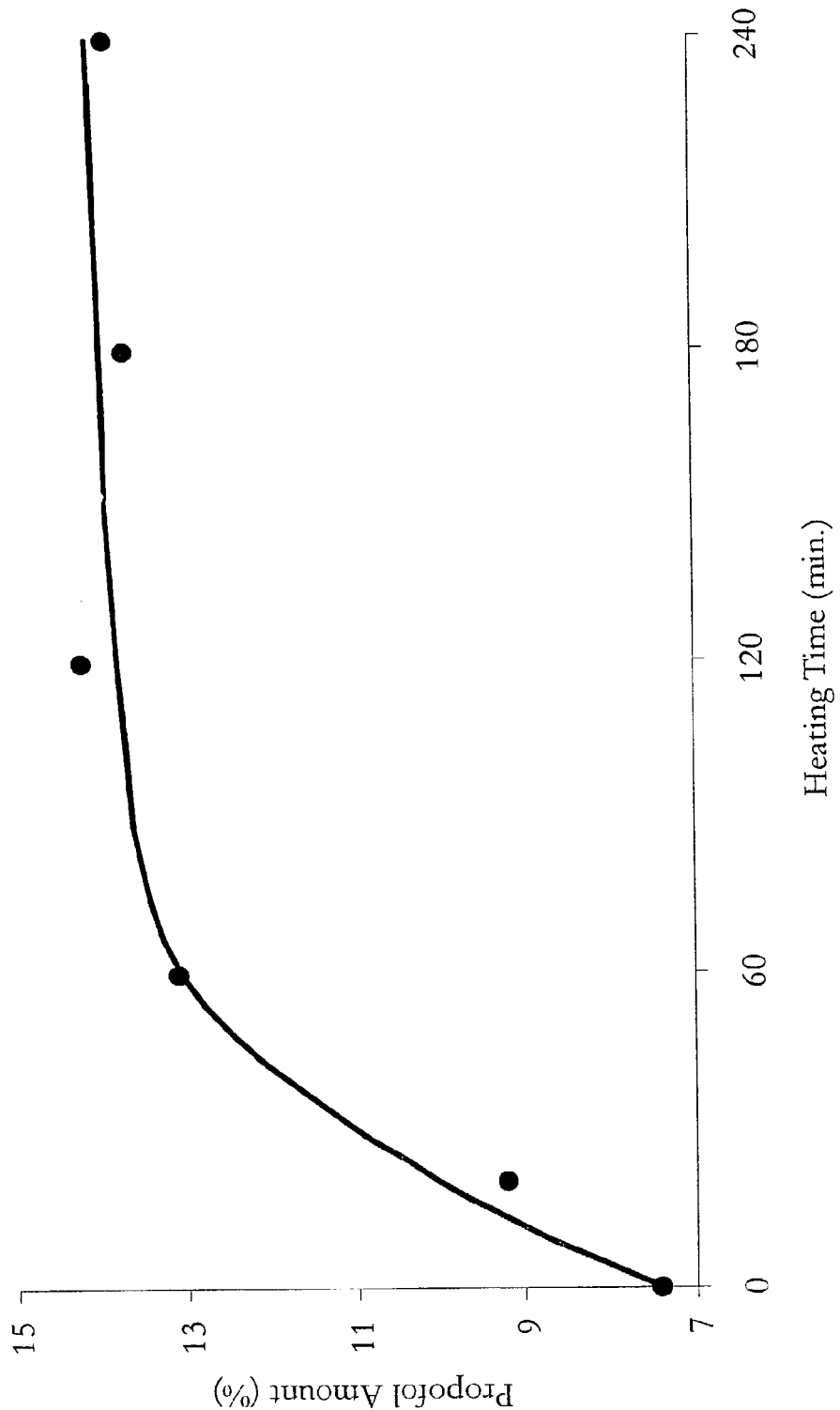
FIG. 4 is a curve showing the effect on propofol as heating time is increased.

The curve shown in FIG. 4 demonstrates that the amount of propofol in liposome increases rapidly as temperature in the first 60 minues, then it converged.

Some propofol emulsion solution with several formulation at different processes (T, A, B and C) were studied. The microbial growth retardation of these propofol emulsions are tested and summarized in Table 7 as follows.

Note: formulation #3 in Table 7 provide a base for microbial growth retardation, however processes A, B and C will provide better retardation for *E. coli* and *P. aeruginosa*. For formulation #4 the same results were observed.

TABLE 7

Comparison of Different Processes on Microbial Growth Retardation

| Formulation | Formulation #1 | Formulation #2 | Formulation #3 | | | | Formulation #4 | |
| --- | --- | --- | --- | --- | --- | --- | --- | --- |
| Propofol, mg/mL | 10 | 10 | 10 | | | | 20 | |
| Soybean Oil, mg/mL | 100 | 100 | 50 | | | | 100 | |
| Egg Lecithin, mg/mL | 12 | 12 | 6 | | | | 12 | |
| EDTA, mg/mL | — | 0.05 | — | | | | — | |
| Process | T | T | T | A | B | C | T | C |
| pH | 8.0 | 8.0 | 6.5 | 6.5 | 6.5 | 6.5 | 8.0 | 6.5 |
| *E. coli*, inoculated CFU | 81 | 47 | 52-68 | 77 | 47 | 54-123 | 81 | 81 |
| Replica | 10 | 10 | 9 | 10 | 30 | 60 | 10 | 10 |
| Ave. Δlog, 24 hrs | >1.57 | −0.85 | −0.05 | −1.07 | −0.34 | −0.54 | >1.57 | −0.52 |
| No. failed | 10 | 0 | 3 | 0 | 0 | 0 | 10 | 0 |

TABLE 7-continued

Comparison of Different Processes on Microbial Growth Retardation

| Formulation | Formulation #1 | Formulation #2 | | Formulation #3 | Formulation #4 |
|---|---|---|---|---|---|
| *P. aeruginosa*, inoculated CFU | | 50 | 38-71 | 50 | 23-77 |
| Replica | | 10 | 6 | 30 | 50 |
| Ave. Δlog, 24 hrs | | −0.29 | −0.78 | −1.67 | −1.45 |
| No. failed | | 0 | 1 | 0 | 0 |

Formulations listed in Table 7 have provided a base to meet microbial growth retardation, however, they need suitable processes to reach the best distribution of propofol, especially in liposome particles.

In a preferred embodiment, the present invention includes a process for the manufacture of a propofol emulsion capable of microbial growth retardation action without the supplementary additives. In particular the activation of the phenol properties of the propofol by the process to entrap a sufficient amount of propofol into the liposomes naturally, or by accelerating the migration of propofol into the liposomal shell. This movement sets up an equilibrium where the propofol makes microorganism growth within all three components of the emulsion unfavorable. Such a reduction in microbial growth will improve the safety of patients using a propofol emulsion that has completed the process detailed herein.

From the foregoing description, the important role of the liposome on microbial growth retardation will be apparent as disclosed herein. Some of the processes to establish or accelerate the equilibrium of propofol between the aqueous phase and liposomes have been described above. Also, modifications can be made to the process without departing from the details of the current invention.

While the invention has been described in complete detail and pictorially shown in the accompanying drawings it is not to be limited to such details, since many changes and modifications may be made in the invention without departing from the spirit and scope thereof. Hence, it is described to cover any and all modifications and forms which may come within the language and scope of the appended claims.

The invention claimed is:

1. A process for obtaining a sterile pharmaceutical composition for a solution of propofol emulsion having a microbial growth retardation and comprising emulsion particles, liposome particles and a supporting aqueous phase, wherein said process comprises the following steps:
   a) mix organic phase: propofol, oil and egg lecithin,
   b) mix aqueous phase: water and glycerin,
   c) mix phase a) and phase b), and adjust pH,
   d) entrap sufficient propofol within shells of liposome particles and allow the entrapped propofol in the liposome shells to reach or be close to the equilibrium of the propofol among the emulsion particles, the aqueous phase and the liposome particles,
   e) emulsify by use of a homogenizer,
   f) adjust final volume and pH,
   g) fill, close and seal,
   h) terminally sterilize,
   i) perform a candling procedure, and
   j) package.

2. The process as specified in claim 1 wherein said equilibrium is reached by a pre-mixing of the propofol, a surfactant and a water-immiscible solvent prior to a conventional homogenizing process.

3. The process as specified in claim 1 wherein said equilibrium is reached by a pre-mixing is performed using a high speed agitator or a high speed in-line mixer, both operating at a speed of at least 5000 rpm.

4. The process as specified in claim 1 wherein the equilibrium of propofol is reached by an accelerated diffusion and redistribution process.

5. The process as specified in claim 4 wherein said accelerated diffusion and redistribution process is performed by heating the sterile pharmaceutical composition at 40° C. for at least fifteen days.

6. The process as specified in claim 4 wherein said accelerated diffusion and redistribution process is performed by heating the sterile pharmaceutical composition at a temperature of at least 60° C. for at least eighteen hours.

7. The process as specified in claim 6 wherein said accelerated diffusion and redistribution process is performed by heating the sterile pharmaceutical composition at a temperature of at least 100° C. for at least one hour.

8. The process as specified in claim 4 wherein the accelerated diffusion and redistribution process is combined with the terminal sterilizing.

9. The process as specified in claim 1 wherein said microbial growth retardation is a result of the propofol and its distribution among the emulsion particles, the aqueous phase and the liposome particles.

* * * * *